United States Patent [19]

Kotacka

[11] 4,007,013
[45] Feb. 8, 1977

[54] HOLDER DEVICE FOR SAMPLE VIALS OR THE LIKE FOR AN ANALYSIS APPARATUS

[75] Inventor: Karl Kotacka, Zurich, Switzerland

[73] Assignee: Contraves AG, Zurich, Switzerland

[22] Filed: July 9, 1976

[21] Appl. No.: 703,844

[30] Foreign Application Priority Data

Sept. 22, 1975 Switzerland .................... 12276/75

[52] U.S. Cl. .................................. 23/259; 233/26
[51] Int. Cl.² ..................... G01N 33/16; B01L 9/06
[58] Field of Search ......... 23/259, 253, 292, 230 B; 233/26

[56] References Cited

UNITED STATES PATENTS

| | | | |
|---|---|---|---|
| 2,447,330 | 8/1948 | Grebmeier | 233/26 |
| 2,834,541 | 5/1958 | Szent-Gyorgyl et al. | 233/26 |
| 3,071,316 | 1/1963 | Piemonte et al. | 23/259 X |

Primary Examiner—R.E. Serwin
Attorney, Agent, or Firm—Werner W. Kleeman

[57] ABSTRACT

A holder device for sample vials or the like for an analysis apparatus, especially a blood cell counter, equipped with a suction tube immersible in a sample vial filled with liquid and standing upon an appropriately arranged support surface in order to remove sample from the sample vial. The holder device has a recess or cavity formed by a rear wall extending approximately parallel to the central axis of the recess and two side walls extending between the lower edge and the upper edge of the holder device and tapering upwardly with respect to the rear wall between the lower edge and the upper edge. The recess is bounded by a standing surface arranged transversely with respect to the rear wall.

7 Claims, 4 Drawing Figures

HOLDER DEVICE FOR SAMPLE VIALS OR THE LIKE FOR AN ANALYSIS APPARATUS

BACKGROUND OF THE INVENTION

The present invention relates to a new and improved construction of a holder device for sample vials, flasks, bottles or the like —hereinafter simply referred to as sample vials— for an analysis device, especially arranged at a blood cell counting device having a suction tube which, for sample removal purposes, is immersible in a sample vial filled with liquid and standing upon a suitably arranged support or standing surface.

German patent publication No. 2,026,759 discloses a blood cell-washing device constructed as a centrifuge and contains, among other things, a rotatable tube carrier head for supporting small sample tubes and equipped with a row of circumferentially distributed openings and recesses which extend downwardly from the surface of the head and possess an essentially vertical outer boundary surface and an upwardly and inwardly inclined inner surface. The construction and angle of inclination of the inner surface is chosen such that during operation there is ensured for a tilting movement of the sample tube located in the recess and the sample tubes, during a certain rotational speed, bear approximately perpendicularly at the inner edge of the boundary surface.

Furthermore, it is known in the case of an analysis device for the determination of the erythrocyte- and leukocyte- count to place a vessel filled with a suitable liquid upon a plate provided with a recess configured in accordance with the vessel in order to secure the same. The plate is guided by at least two guide rods attached to the housing of the analysis device. After placement of the vessel upon the plate it is then manually brought into engagement with a suction needle, and the plate either is held in this position by slightly tilting the same at both guide rods or, however is manually held in this position until the counting operation is completed.

Also known in the art is a blood cell counter wherein, for preparing the sample vial filled with the sample to be analyzed, a suction needle is slightly bent manually by using one hand and with the other hand the sample vial is brought into a desired position to remove sample therefrom and placed upon a support surface. When changing to a different sample this operation must be carried out in a reverse sequence. With this blood cell counter care must be taken that the suction needle is not bent too strongly, otherwise due to snapping back of the needle, liquid will be propelled outwardly and, consequently, air will enter the measuring system. Additionally, the need to operate the device with both hands is disadvantageous.

SUMMARY OF THE INVENTION

Hence, it is a primary object of the present invention to provide an improved construction of holder device for sample vials or the like for use with an analysis apparatus which is not associated with the aforementioned drawbacks and limitations of the prior art proposals.

Another and more specific object of the present invention is directed to the provision of a holder device for sample vials or the like for an analysis apparatus equipped, for instance, with a fixed suction tube, wherein, with a single manipulation, it is possible to bring a sample vial sufficiently filled with a sample medium for carrying out at least two measurements into a position for removal of the sample without any sample loss, and wherein preferably the central axis of the suction tube approximately coincides with the central axis of the sample vial.

Yet a further significant object of the present invention aims at the provision of a novel holder device for sample vials for use with analysis apparatus wherein the sample vial can be placed easily, without any complicated manipulations, into a position where it is securely supported by the holder device for permitting removal of a sample from the vial to carry out the analysis.

Now in order to implement these and still further objects of the invention, which will become more readily apparent as the description proceeds, the holder device of this invention is provided with a recess or cavity which is bounded by a rear wall extending approximately parallel to the central axis of the recess as well as by two side walls extending from the lower edge up to the upper edge of the holder device. The side walls in relation to the rear wall taper from the lower edge upwardly towards the upper edge, and further, the recess is bounded by a support or standing surface arranged transversely with respect to the rear wall.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
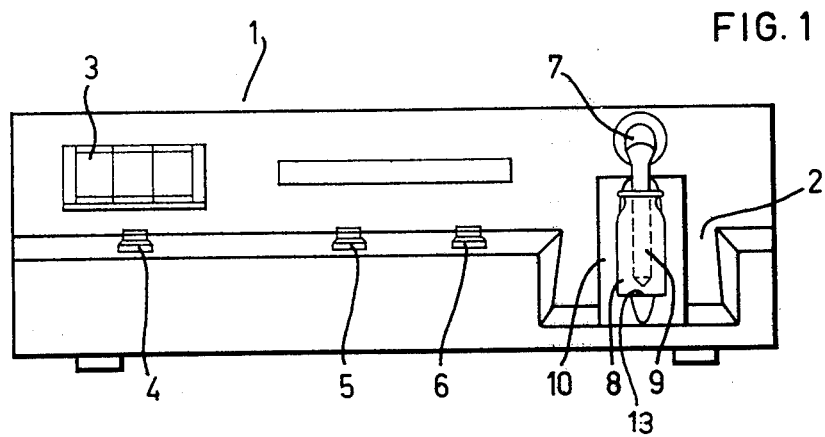
FIG. 1 is a front view of an analysis apparatus equipped with a holder device and showing the sample vial or the like mounted thereat.

Describing new the drawings, in FIG. 1 there is shown by way of example an analysis apparatus constituting a blood cell counting device 1 which has been shown in front view. There will be recognized the individual operating elements, wherein reference character 4 is a switch- on or start button, reference character 5 a measuring button for the leukocyte count, reference character 6 a measuring button for the erythrocyte count, and reference character 3 a result indicator for indicating or displaying the momentary counting result. As should be apparent details of the operation of the blood cell counting device or counter are unnecessary for understanding the underlying concepts of the invention since the same is directed to the holder device for mounting a sample vial or the like at the analysis device.

Further, it will be recognized a measuring head 7 is arranged above a corner or pocket 2 provided at the front surface of the apparatus 1, this front surface preferably inclining upwards and rearwards from the bottom of the apparatus 1. Measuring head 7 is provided for instance with a fixed suction tube 9 which can be immersed into a sample vial 8 during such time as the sample vial 8 is securely standing upon a support or standing surface 13 of a holder device 10 constituting the subject matter of the invention. Retention of the sample vial 8 securely at the holder device 10 is possible without the need to resort to any additional holding- or clamping elements.

Figure 2:
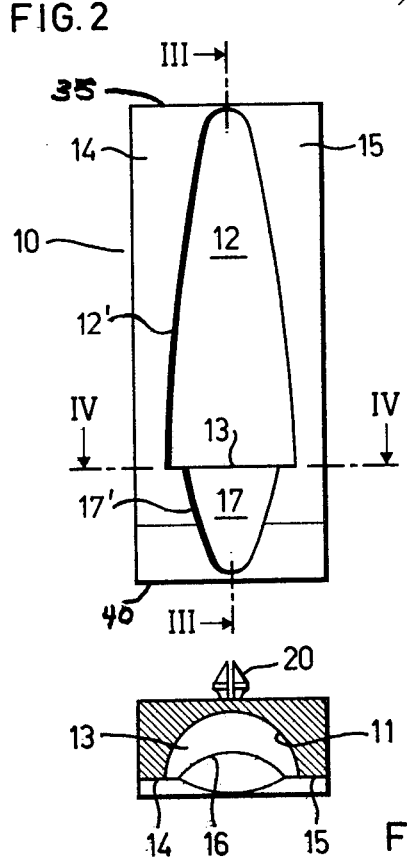
FIG. 2 is an enlarged front view of the holder device used in the arrangement of FIG. 1.
Figure 3:
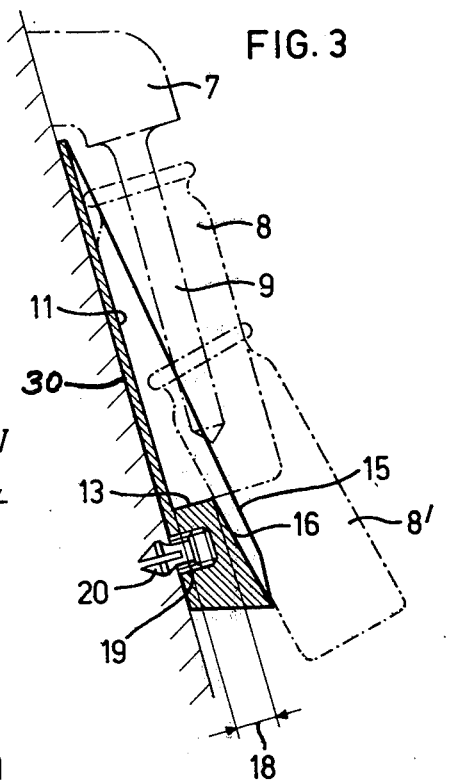
FIG. 3 is a side sectional view of the holder device illustrated in FIG. 2 taken along the line III—III thereof and depicting the insertion- and mounted or final-position of the sample vial.
Figure 4:
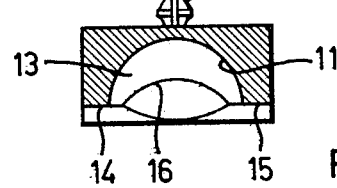
FIG. 4 is a cross-sectional plan view of the holder device illustrated in FIG. 2 taken substantially along the line IV — IV thereof.

Reference now will be made to FIGS. 2, 3 and 4 which shows on an enlarged scale details of the holder device 10 of the invention, wherein in FIG. 3 there has been illustrated in phantom lines both the position of the sample vial 8 when it is mounted for removal of the sample contained therein at the holder device and such sample vial, here designated by reference character 8', during such time as it is being introduced into the holder device.

FIG. 2 illustrates the holder device 10 in front view and there will be seen a holder body 30 having a recess 12 enclosed by two for instance flat side walls 14 and 15. This recess or cavity 12 extends from the upper edge 35 of the holder device 10 to the standing or support surface 13. Further, recess 12 is provided with a rear wall 11 serving as a contact or support surface for the sample vial 8 as well as a recess 17 extending from the lower edge 40 of the holder device 10 to the support or standing surface 13. The recess or cavity 17 has a wall 16 serving as a slide surface to assist in sliding the vial into the vial receiving-recess 12 of the holder device 10. The recesses 12 and 17, in the illustrated exemplary embodiment, are formed from an inclined, cut or bevelled, cylindrical bore, wherefore the cut edges of the recesses bounding at the side walls 14 and 15 appear as approximately parabolic edges 12' and 17' respectively. A different configuration, for instance a polygonal shape of the recesses 12 and 17 is equally possible and can be carried out without any great difficulty.

FIG. 3 illustrates the holder device 10 in sectional view and the inclined front surface of the analysis apparatus 1. There will be recognized the suction tube 9 of the measuring head 7 which expands approximately parallel to the rear wall 11 and is immersed in the sample vial 8. To accomplish the measuring operation the sample vial 8' shown in phantom lines in FIG. 3 and which has been filled to a certain level or height with the sample or medium, for instance sufficient to carry out two measurements, is inclined slightly and guided from below while bearing against the wall 16 into the recess 17, pushed upwardly and placed upon the support or standing surface 13. In this position which is required to carry out the measurement operation, the sample vial 8 bears firmly and securely against the inclined rear wall 11 and the suction tube 9 is located with its central or lengthwise axis at the central or lengthwise axis of the sample vial, so that no contact occurs between the suction tube and the sample vial, and thus, there is ensured for a faultless suction operation. The depth or width 18 of the standing or support surface 13 is calculated so that it is not greater than the radius of the sample vial 8, which, in the illustrated example, has been assumed to be cylindrical in shape; but it should be understood that when using other shapes of vials the depth 18 is to be appropriately dimensioned.

By virtue of the side walls 14 and 15 which extend upwardly at an inclination the sample vial 8, which bears at the rear wall 11, is sufficiently free at its upper region so that there is ensured for an optimum secure grasping of such sample vial.

At the side confronting the front surface of the apparatus 1 the holder device 10 is preferably provided with a threaded blindhole bore 19 for receiving a clamping plug or pin 20, for instance an expansible plug, so that holder device 10 can be easily exchangeably mounted and subsequently also can by installed at other analysis apparatuses.

FIG. 4 illustrates a section, taken along the line IV — IV of FIG. 2, of the holder device 10 of the invention. There will be recognized the rear wall 11 of the recess 12 formed, for instance, of approximately semi-circular shape and bounded by both side walls 14 and 15. There also will be seen the standing or support surface 13 and the arcuate-shaped wall 16 of the recess 17.

According to a variant construction of the invention it is possible to fabricate the front plate of the analysis apparatus from plastic by injection molding or deep-drawing techniques and to provide at a suitably arranged corner or region the important features of the sample vial holding- and receiving recess 12, the standing surface 13, recess 17 and both of the lateral side walls 14, 15 which extend upwards at an inclination.

While there are shown and described present preferred embodiments of the invention, it is to be distinctly understood that the invention is not limited thereto, but may be otherwise variously embodied and practiced within the scope of the following claims. ACCORDINGLY,

I claim:

1. A holder device for sample vials for an analysis apparatus, especially a blood cell counter, equipped with a suction tube which can be immersed in a sample vial filled with a liquid sample for removing the sample therefrom, comprising a holder body having means defining a recess for receiving and holding a sample vial, said means defining said recess comprising a rear wall extending approximately parallel to the central axis of the recess and two side walls extending from a lower edge to an upper edge of the holder body, said two side walls upwardly tapering with regard to the rear wall from the lower edge to the upper edge, and a standing surface for the sample vial arranged transversely with respect to the rear wall.

2. The holder device as defined in claim 1, wherein the standing surface has a depth which does not exceed the radius of the sample vial.

3. The holder device as defined in claim 1, wherein the rear wall of the recess comprises a substantially cylindrical bore.

4. The holder device as defined in claim 1, further including a substantially arcuate-shaped rear wall having a recess means corresponding to said recess and extending from the lower edge of the holder body up to the standing surface.

5. The holder device as defined in claim 4, wherein said recess means is substantially in alignment with said recess.

6. The holder device as defined in claim 1, further including at least one clamping plug provided for the holder body for mounting thereof at the analysis apparatus.

7. A holder device for sample vials for an analysis apparatus, especially a blood cell counter, equipped with a suction tube which can be immersed in a sample vial filled with a liquid sample for removing the sample therefrom, comprising a holder body having means defining a recess for receiving and holding a sample vial, said means defining said recess comprising a rear wall and two side walls extending between a lower edge and an upper edge of the holder body, said two side walls upwardly converging with regard to the rear wall between the lower edge and the upper edge, and a standing surface for the sample vial arranged transversely with respect to the rear wall.

* * * * *